United States Patent
Yashiro et al.

(10) Patent No.: US 9,738,619 B2
(45) Date of Patent: Aug. 22, 2017

(54) 2,5-FURAN DICARBOXYLIC ACID PRODUCTION METHOD

(71) Applicant: KAO CORPORATION, Tokyo (JP)

(72) Inventors: Kai Yashiro, Wakayama (JP); Masato Nomura, Wakayama (JP); Kaoru Ohmae, Iwade (JP); Yukiko Tabuchi, Wakayama (JP)

(73) Assignee: KAO CORPORATION, Tokyo (JP)

( * ) Notice: Subject to any disclaimer, the term of this patent is extended or adjusted under 35 U.S.C. 154(b) by 0 days.

(21) Appl. No.: 15/021,997

(22) PCT Filed: Aug. 26, 2014

(86) PCT No.: PCT/JP2014/072328
§ 371 (c)(1),
(2) Date: Mar. 15, 2016

(87) PCT Pub. No.: WO2015/041013
PCT Pub. Date: Mar. 26, 2015

(65) Prior Publication Data
US 2016/0221979 A1 Aug. 4, 2016

(30) Foreign Application Priority Data
Sep. 19, 2013 (JP) ................................ 2013-193967

(51) Int. Cl.
C07D 307/68 (2006.01)
(52) U.S. Cl.
CPC .................... C07D 307/68 (2013.01)
(58) Field of Classification Search
None
See application file for complete search history.

(56) References Cited

U.S. PATENT DOCUMENTS 4,977,283 A * 12/1990 Leupold ............... C07D 307/68 549/484
2008/0103318 A1 5/2008 Lilga et al.
2013/0137882 A1 5/2013 Borsotti et al.

FOREIGN PATENT DOCUMENTS

| CN | 101891719 A | 11/2010 |
|---|---|---|
| JP | 62-269746 A | 11/1987 |
| JP | 2008-88134 A | 4/2008 |
| JP | 2009-29759 A | 2/2009 |
| JP | 2013-203666 A | 10/2013 |
| WO | WO 01/72732 A2 | 10/2001 |
| WO | WO 0172732 A2 * | 10/2001 ........... C07D 307/36 |
| WO | WO 2008/054804 A2 | 5/2008 |
| WO | WO 2013/146085 A1 | 10/2013 |

OTHER PUBLICATIONS

Casanova et al., "Biomass into Chemicals: Aerobic Oxidation of 5-Hydroxy-methyl-2-furfural into 2,5-Furandicarboxylic Acid with Gold Nanoparticle Catalysts", ChemSusChem 2009, 2, pp. 1138-1144.
International Search Report for PCT/JP2014/072328 mailed on Sep. 30, 2014.
Rass et al., "Selective aqueous phase oxidation of 5-hydroxymethylfurfural to 2,5-furandicarboxylic acid over Pt/C catalysts: influence of the base and effect of bismuth promotion†", Green Chemistry, vol. 15, RSCPublishing, The Royal Society of Chemistry 2013, p. 2240 (12 pages).
Vinke et al., "Platinum catalyzed oxidation of 5-hydroxymethylfurfural", New Developments in Selective oxidation, 1990, pp. 147-158.
Davis et al., "Oxidation of 5-hydroxymethylfurfural over supported Pt, Pd and Au catalysts," Catalysis Today, vol. 160, No. 1, Feb. 2, 2011 (available online Jul. 7, 2010), pp. 55-60.
Extended European Search Report, dated Mar. 28, 2017, for European Application No. 14845684.1.
Gorbanev et al., "Selective aerobic oxidation of 5-hydroxymethylfurfural in water over solid ruthenium hydroxide catalysts with magnesium-based supports," Catalysis Letters, vol. 141, No. 12, 2011 (published online Oct. 1, 2011), pp. 1752-1760.
Villa et al., "Pd-modified Au on carbon as an effective and durable catalyst for the direct oxidation of HMF to 2,5-furandicarboxylic acid," ChemSusChem, vol. 6, No. 4, 2013 (published online Mar. 11, 2013), pp. 609-612.

* cited by examiner

Primary Examiner — Heidi Reese
(74) Attorney, Agent, or Firm — Birch, Stewart, Kolasch & Birch, LLP

(57) ABSTRACT

The present invention relates to a process for producing 2,5-furan dicarboxylic acid by subjecting 5-hydroxymethylfurfural to oxidation reaction in the presence of water, oxygen and an activated carbon-supported metal catalyst containing a noble metal, the process including the following steps (1) and (2) in which the steps (1) and (2) are carried out under a pressure of not less than 0.1 MPa and less than 1.0 MPa while maintaining a reaction solution at a pH of not more than 7, and an amount of the oxygen fed until a time at which the step (2) is terminated is not less than 120 mol % and not more than 140 mol % on the basis of the 5-hydroxymethylfurfural charged: step (1): conducting the oxidation reaction at a temperature of not lower than 50° C. and not higher than 110° C. until a content of the 5-hydroxymethylfurfural in the reaction solution falls within the range of not less than 0 mg/kg and not more than 1,000 mg/kg; and step (2): subjecting the reaction solution obtained after completion of the step (1) to the oxidation reaction at a temperature of not lower than 140° C. and not higher than 250° C.

20 Claims, No Drawings

2,5-FURAN DICARBOXYLIC ACID PRODUCTION METHOD

FIELD OF THE INVENTION

The present invention relates to a process for producing 2,5-furan dicarboxylic acid.

BACKGROUND OF THE INVENTION 2,5-Furan dicarboxylic acid (hereinafter also referred to as "FDCA") is a useful compound as an intermediate product for fine chemicals or raw materials of synthetic resins, though the compound can be synthesized from fructose (fruit sugar) contained in a large amount in plants. For this reason, FDCA is selected as one of building block chemicals for biorefinery which have been identified by The US Department of Energy.

FDCA is highly practically valuable as a monomer for synthetic resins or toner binders or as an intermediate product in various application fields such as medicines, agricultural chemicals, insecticides, antibacterial agents, perfumes and others. Therefore, various studies have been made on the process for production of FDCA.

WO 2008/054804A discloses a method of oxidation of 5-hydroxymethylfurfural (hereinafter also referred to as "HMF") in which oxygen is supplied into an aqueous solution of HMF to subject HMF to oxidation reaction at a temperature of from 50 to 200° C. under a pressure of from 150 to 500 psi (1.03 to 3.45 MPa) in the presence of a catalyst prepared by supporting Pt on a carrier such as $ZrO_2$.

In Onofre Casanova, et al., "ChemSusChem", 2009, Vol. 2, p. 1138, there is disclosed a technology of oxidation reaction for conversion of HMF into FDCA in which HMF and oxygen are fed into an alkali aqueous solution having a pH of 8 to 11 to subject HMF to oxidation reaction in the presence of a catalyst prepared by supporting Au on a $CeO_2$ carrier at 25° C. for 4 h, and then the resulting oxidation reaction product is heated to 130° C. and further reacted under 1.0 MPa for 3 h.

In addition, in Hicham Ait Rass, et al., "Green Chemistry", 2013, Vol. 15, p. 2240, there is disclosed a selective aqueous phase oxidation method for transformation of HMF into FDCA in which HMF is subjected to air oxidation in an alkali aqueous solution having a pH of about 8 to about 11 in the presence of a catalyst prepared by supporting Pt and Bi on activated carbon at 100° C. under 40 bar (4.0 MPa).

SUMMARY OF THE INVENTION

The present invention relates to a process for producing 2,5-furan dicarboxylic acid by subjecting 5-hydroxymethylfurfural to oxidation reaction in the presence of water, oxygen and an activated carbon-supported metal catalyst containing a noble metal, the process including the following steps (1) and (2) in which the steps (1) and (2) are carried out under a pressure of not less than 0.1 MPa and less than 1.0 MPa while maintaining a reaction solution at a pH of not more than 7, and an amount of the oxygen fed until a time at which the step (2) is terminated is not less than 120 mol % and not more than 140 mol % on the basis of the 5-hydroxymethylfurfural charged:

step (1): conducting the oxidation reaction at a temperature of not lower than 50° C. and not higher than 110° C. until a content of the 5-hydroxymethylfurfural in the reaction solution falls within the range of not less than 0 mg/kg and not more than 1,000 mg/kg; and step (2): subjecting the reaction solution obtained after completion of the step (1) to the oxidation reaction at a temperature of not lower than 140° C. and not higher than 250° C.

DETAILED DESCRIPTION OF THE INVENTION

In the technology described in WO 2008/054804A, it is required to conduct the reaction under high-temperature and high-pressure conditions in order to produce FDCA with high yield, and the reaction therefore needs a large energy load and a complicated production apparatus. Also, the technology described in WO 2008/054804A tends to have such a problem that Pt in the catalyst is eluted into the reaction solution. In order to compensate deterioration in catalytic activity of the catalyst owing to the elution of Pt, it is required to use a large amount of expensive Pt and further carry out a step of recovering Pt thus eluted, thereby posing problems such as low productivity and poor economy.

Further, in the technologies described in Onofre Casanova, et al., "ChemSusChem", 2009, Vol. 2, p. 1138, and Hicham Ait Rass, et al., "Green Chemistry", 2013, Vol. 15, p. 2240, since the oxidation reaction is carried out in the alkali aqueous solution, FDCA as the target product is produced in the form of an alkali salt thereof. For this reason, the above technologies inevitably need a desalting treatment after completion of the reaction and therefore tend to suffer from problems owing to a large burden of the additional treatment.

The present invention aims at providing a process for producing 2,5-furan dicarboxylic acid from 5-hydroxymethylfurfural with high productivity in an industrially useful manner.

The present inventors have found that the above problems can be solved by conducting the oxidation reaction in two-stage temperature ranges at a pH of not more than 7 under near normal pressures using an activated carbon-supported metal catalyst containing a noble metal.

That is, the present invention provides a process for producing 2,5-furan dicarboxylic acid by subjecting 5-hydroxymethylfurfural to oxidation reaction in the presence of water, oxygen and an activated carbon-supported metal catalyst containing a noble metal, the process including the following steps (1) and (2) in which the steps (1) and (2) are carried out under a pressure of not less than 0.1 MPa and less than 1.0 MPa while maintaining a reaction solution at a pH of not more than 7, and an amount of the oxygen fed until a time at which the step (2) is terminated is not less than 120 mol % and not more than 140 mol % on the basis of the 5-hydroxymethylfurfural charged:

step (1): conducting the oxidation reaction at a temperature of not lower than 50° C. and not higher than 110° C. until a content of the 5-hydroxymethylfurfural in the reaction solution falls within the range of not less than 0 mg/kg and not more than 1,000 mg/kg; and step (2): subjecting the reaction solution obtained after completion of the step (1) to the oxidation reaction at a temperature of not lower than 140° C. and not higher than 250° C.

According to the present invention, it is possible to produce 2,5-furan dicarboxylic acid from 5-hydroxymethylfurfural with high productivity in an industrially useful manner.

[Process for Producing 2,5-Furan Dicarboxylic Acid]

The process for producing 2,5-furan dicarboxylic acid according to the present invention is characterized by such a process for producing 2,5-furan dicarboxylic acid by subjecting 5-hydroxymethylfurfural to oxidation reaction in the presence of water, oxygen and an activated carbon-supported metal catalyst containing a noble metal, the process including the following steps (1) and (2) in which the steps (1) and (2) are carried out under a pressure of not less than 0.1 MPa and less than 1.0 MPa while maintaining a reaction solution at a pH of not more than 7, and an amount of the oxygen fed until a time at which the step (2) is terminated is not less than 120 mol % and not more than 140 mol % on the basis of the 5-hydroxymethylfurfural charged:

step (1): conducting the oxidation reaction at a temperature of not lower than 50° C. and not higher than 110° C. until a content of the 5-hydroxymethylfurfural in the reaction solution falls within the range of not less than 0 mg/kg and not more than 1,000 mg/kg; and step (2): subjecting the reaction solution obtained after completion of the step (1) to the oxidation reaction at a temperature of not lower than 140° C. and not higher than 250° C.

Meanwhile, the "5-hydroxymethylfurfural charged" as used herein means a total amount of the 5-hydroxymethylfurfural used as the raw material.

The reason why the production process of the present invention is capable of producing FDCA with high productivity in an industrially useful manner is considered as follows.

That is, HMF as a raw material of FDCA tends to readily undergo thermal decomposition, so that there tends to occur such a problem that the increase in temperature of the reaction causes production of by-products. On the other hand, FDCA as the target product has a low water solubility and therefore can be hardly enhanced in its concentration in the reaction system at a low temperature, and the catalyst used therein is deteriorated in catalytic activity for the oxidation reaction of HMF at the low temperature, thereby causing problems such as poor productivity. In addition, in the high-temperature reaction system in which the water solubility of FDCA can be enhanced, the resulting FDCA tends to be reacted with oxygen to produce by-products, which also results in problems such as poor productivity. As the method of enhancing water solubility of FDCA even in the low-temperature reaction system, there is effectively used a method of conducting the reaction in an alkali aqueous solution. However, in such a method, it is inevitably required to conduct an additional treatment such as desalting treatment.

In consequence, in the production process of the present invention, first, HMF is subjected to oxidation reaction in the presence of an activated carbon-supported metal catalyst in a low temperature range of not lower than 50° C. and not higher than 110° C. in which HMF is comparatively stable, and then at the time at which the concentration of HMF in the reaction system reaches 1,000 mg/kg or lower, the reaction solution is heated to a high temperature range of not lower than 140° C. and not higher than 250° C., so that FDCA can be enhanced in solubility and prevented from being decomposed while increasing activity for the oxidation reaction. Further, it is considered that by controlling a total amount of the oxygen fed from initiation of charging the raw material to termination of the step (2) to not less than 120 mol % and not more than 140 mol % on the basis of HMF charged, it is possible to suppress production of by-products in the step (2) and efficiently convert HMF into FDCA.

In addition, in the present invention, the oxidation reaction is conducted under a pressure as low as less than 1.0 MPa, so that facility investment is lowered, and the process therefore becomes industrially advantageous.

<5-Hydroxymethylfurfural>

The 5-hydroxymethylfurfural (HMF) used in the present invention can be synthesized from sugars as a raw material, for example, by the method described in WO 2013/146085A. The sugars as the raw material used in the present invention may be either natural substance-derived sugars, artificially synthesized sugars or a mixture of these sugars.

(Sugars as Raw Material)

Specific examples of the sugars as the raw material include at least one sugar selected from the group consisting of a monosaccharide, a disaccharide, an oligosaccharide and a polysaccharide. In addition, as the sugars as the raw material, there may be used a sugar solution derived from starch, cane, sugar beet, soybean, etc., which are in the form of a mixture containing the above sugars, and a refined intermediate product and a refined by-product obtained from the sugar solution, for example, high fructose corn syrup, refined sugar, raw sugar, molasses, invert sugar and isomerized sugar, etc. Of these sugars as the raw material, from the viewpoint of producing FDCA in an economical efficient manner, preferred are sugars containing fructose.

As the sugars containing fructose, from the viewpoint of high yield of FDCA, there are preferably used fructose, a disaccharide obtained by combining fructose with an optional monosaccharide, an oligosaccharide obtained by combining fructose with an optional monosaccharide, a polysaccharide obtained by combining fructose with an optional monosaccharide, and high fructose corn syrup. Also, as the sugars containing fructose, from the same viewpoint as described above, there are preferably used refined intermediate product and by-product of the aforementioned monosaccharide, disaccharide, oligosaccharide, polysaccharide and high fructose corn syrup. Further, as the sugars containing fructose, from the same viewpoint as described above, there are preferably used a soybean sugar solution, and a sugar solution derived from cane or sugar beet. In addition, as the sugars containing fructose, from the same viewpoint as described above, there are preferably used refined sugar, raw sugar, molasses and invert sugar obtained from the soybean sugar solution or the sugar solution derived from cane or sugar beet; and inulin. Of these sugars containing fructose, more preferred are a mixture of glucose and fructose, refined sugar, raw sugar, molasses, fructose, sucrose, and inulin.

(Concentration of HMF)

In the production process of the present invention, the content of HMF in a whole amount of the reaction solution upon initiation of the reaction in the step (1) is not particularly limited. From the viewpoint of improving solubility of the resulting reaction product and yield of FDCA, the content of HMF in a whole amount of the reaction solution is preferably not less than 0.5% by mass, more preferably not less than 1.0% by mass, even more preferably not less than 2.0% by mass, and further even more preferably not less than 3.0% by mass, and is also preferably not more than 8.0% by mass, more preferably not more than 7.0% by mass, even more preferably not more than 6.0% by mass, and further even more preferably not more than 5.0% by mass.

<Activated Carbon-Supported Metal Catalyst)

The activated carbon-supported metal catalyst used in the present invention (hereinafter also referred to merely as a "metal catalyst" or a "catalyst") means a catalyst prepared by supporting metal components such as a noble metal (hereinafter also referred to merely as "metal components") on the activated carbon. The metal components may also contain metals other than the noble metal.

(Metal Components)

[Noble Metal]

The noble metal is a transition metal belonging to Groups 8 to 11 of Periods 5 to 6 of the Periodic Table. Specific examples of the noble metal include at least one element selected from the group consisting of gold (Au), silver (Ag), platinum (Pt), palladium (Pd), iridium (Ir), rhodium (Rh), osmium (Os) and ruthenium (Ru). Of these noble metals, from the viewpoint of improving reaction rate and yield of FDCA, preferred is at least one element selected from the group consisting of platinum group metals such as Pt, Pd, Ir, Rh, Os and Ru which belong to Groups 8 to 11 of Periods 5 to 6 of the Periodic Table, and more preferred is Pt.

The amount of the noble metal supported on the activated carbon-supported metal catalyst is not particularly limited. From the viewpoint of improving yield of FDCA and economy, the amount of the noble metal supported on the activated carbon-supported metal catalyst is preferably not less than 0.5% by mass, more preferably not less than 1% by mass, even more preferably not less than 2% by mass, and further even more preferably not less than 3% by mass, and is also preferably not more than 15% by mass, more preferably not more than 10% by mass, even more preferably not more than 8% by mass, and further even more preferably not more than 7% by mass, on the basis of a whole amount of the catalyst.

[Metal (A)]

From the viewpoints of high yield of FDCA and good durability of the catalyst, the metal catalyst preferably contains at least one metal (A) selected from the group consisting of bismuth (Bi) and tin (Sn), and more preferably bismuth, as the second metal component.

The mass ratio of the noble metal to the metal (A) [noble metal/metal (A)] in the catalyst is not particularly limited. From the viewpoint of improving yield of FDCA and durability of the catalyst, the mass ratio of the noble metal to the metal (A) [noble metal/metal (A)] in the catalyst is preferably not less than 1, more preferably not less than 2, even more preferably not less than 3, and further even more preferably not less than 4, and is also preferably not more than 10, more preferably not more than 9, even more preferably not more than 8, further even more preferably not more than 7, and further even more preferably not more than 6.

[Metal (B)]

From the viewpoint of suppressing progress of side reactions of HMF and FDCA, the metal catalyst may further contains at least one metal (B) selected from the group consisting of Cu and Ni as the third metal component.

The mass ratio of the metal (A) to the metal (B) [metal (A)/metal (B)] in the catalyst is not particularly limited. From the viewpoints of improving yield of FDCA and suppressing progress of the side reactions, the mass ratio of the metal (A) to the metal (B) [metal (A)/metal (B)] in the catalyst is preferably not less than 0.2, more preferably not less than 0.4, even more preferably not less than 0.6, and further even more preferably not less than 0.8, and is also preferably not more than 5.0, more preferably not more than 3.0, even more preferably not more than 1.5, and further even more preferably not more than 1.2.

<Activated Carbon>

The activated carbon acts as a carrier for the catalyst which serves for enhancing dispersibility of the metal components and improving reactivity thereof. However, it is considered that the activated carbon is also interacted with a reaction substrate and exhibits an effect or a function of attracting the reaction substrate to the catalyst owing to the interaction to promote an oxidation reaction thereof.

In the present invention, there may be used conventionally known activated carbons. Examples of a raw material of the activated carbon include plant-based raw materials such as timber, sawdust, charcoal, carbon ash, fruit shells such as coconut shell and walnut shell, seeds of fruits such as peach and prunus mume, fruit shell charcoal, fruit seed charcoal, by-products generated upon production of pulps, lignin waste liquid, sugar production wastes and molasses; mineral-based raw materials such as peat, grass peat, lignite, brown coal, bituminous coal, anthracite, coke, coal tar, coal pitch, petroleum distillation residues and petroleum pitch; natural materials such as seaweed and rayon; and synthetic materials such as phenol resins, vinylidene chloride resins and acrylic resins.

Of these materials, from the viewpoints of cost-efficiency and well controlling a structure of the activated carbon, preferred are mineral-based raw materials such as peat, grass peat, lignite, brown coal, bituminous coal, anthracite, coke, coal tar, coal pitch and petroleum pitch; and synthetic materials such as phenol resins, vinylidene chloride resins and acrylic resins.

As the method of activating the activated carbon, there may be used, for example, a gas-activation method using water vapor, a carbon dioxide gas, a combustion gas, air or the like, and a chemical-activation method using zinc chloride, phosphoric acid, potassium carbonate, calcium chloride or the like, though it is not particularly limited thereto.

Examples of the configuration of the activated carbon include, but are not particularly limited to, a powder shape, a granular shape, a fiber shape, a cylindrical shape, a honeycomb shape or the like. From the viewpoints of good workability upon preparation of the catalyst and good dispersibility in the reaction solution, the configuration of the activated carbon is preferably a powder shape or a granular shape, and more preferably a powder shape.

(Specific Surface Area of Activated Carbon)

From the viewpoints of enhancing dispersibility of the metal components and improving reaction rate and yield of FDCA as well as durability of the catalyst, the specific surface area of the activated carbon is preferably not less than 600 $m^2/g$, more preferably not less than 700 $m^2/g$, even more preferably not less than 800 $m^2/g$, and further even more preferably not less than 900 $m^2/g$, and is also preferably not more than 3000 $m^2/g$, more preferably not more than 2500 $m^2/g$, even more preferably not more than 2000 $m^2/g$, and further even more preferably not more than 1500 $m^2/g$, though it is not particularly limited thereto. Meanwhile, the specific surface area may be measured by the method described in Examples below.

(Pore Volume of Activated Carbon)

From the viewpoints of enhancing dispersibility of the metal components and improving reaction rate and yield of FDCA as well as durability of the catalyst, the pore volume of the activated carbon is preferably not less than 0.4 $cm^3/g$, more preferably not less than 0.5 $cm^3/g$, even more preferably not less than 0.6 $cm^3/g$, and further even more preferably not less than 0.7 $cm^3/g$, and is also preferably not more than 5.0 cm³/g, more preferably not more than 3.0 cm³/g, even more preferably not more than 2.0 cm³/g, and further even more preferably not more than 1.0 cm³/g, though it is not particularly limited thereto. The pore volume of the activated carbon may be measured, for example, by known methods such as a gas adsorption method and a mercury-helium method.

<Amount of Activated Carbon-Supported Metal Catalyst Used>

In the production process of the present invention, the amount of the activated carbon-supported metal catalyst used is not particularly limited, and is controlled such that a mass of the noble metal used in the catalyst is preferably not less than 0.5% by mass, more preferably not less than 1% by mass, even more preferably not less than 2% by mass, and further even more preferably not less than 3% by mass, and is also preferably not more than 10% by mass, more preferably not more than 9% by mass, even more preferably not more than 8% by mass, and further even more preferably not more than 7% by mass, on the basis of a mass of HMF, from the viewpoint of satisfying both of high yield of FDCA and cost-efficiency.

<Method for Production of Catalyst>

The activated carbon-supported metal catalyst used in the present invention may be produced by known methods such as the method described in JP 62-269746A. For example, the activated carbon-supported metal catalyst may be produced by the method in which after adsorbing a precursor of the noble metal and, if required, a precursor of the other metal component onto the activated carbon, the resulting material is subjected to reducing treatment.

Examples of the precursor of the respective metal components include a chloride, a fluoride, a bromide, a hydroxide, a nitrate, sulfate, an acetate, a carbonate, an ammonium salt, etc., of the metals. These precursors may be used alone or in the form of a mixture containing any two or more thereof at an optional mixing ratio.

For example, as the precursor of platinum, there may be mentioned platinum chloride, platinum bromide, hexachloroplatinic acid, platinum sulfite, tetraammineplatinum chloride, tetraammineplatinum hydroxide, tetraammineplatinum nitrate, dinitro diamine platinum, etc. Of these precursors of platinum, from the viewpoint of good dispersibility of platinum and cost-efficiency, preferred are hexachloroplatinic acid and tetraammineplatinum chloride.

As the method of adsorbing the respective metal components onto the activated carbon, there may be used, for example, (i) an impregnation method in which after suspending the activated carbon in a solution of the precursor of the metal component, a solvent in the solution is distilled off from the resulting suspension, (ii) a precipitation method in which the precursor solution is contacted with a precipitant to produce a precipitate such as a carbonate of the metal component, (iii) an ion exchange method in which an acid point or a base point of the activated carbon is subjected to ion exchange with a metal ion, (iv) a spray method in which the precursor solution is sprayed onto the activated carbon under reduced-pressure condition, and (v) an incipient wetness method in which after evaluating the activated carbon, the precursor solution is added little by little thereto so as to impregnate the same volume of the precursor solution as a pore volume of the activated carbon thereinto. Of these methods, from the viewpoints of good dispersibility of the metal component and good workability, preferred are the impregnation method, the precipitation method and the ion exchange method, and more preferred are the impregnation method and the precipitation method.

The order of supporting of the respective metal components is not particularly limited. All of a plurality of the metal components may be supported on the activated carbon at the same time, or the individual metal components may be separately supported thereon.

(Reducing Treatment)

After supporting the metal components on the activated carbon by any of the aforementioned methods, the resulting catalyst may be subjected to drying and reducing treatments to prepare the activated carbon-supported metal catalyst. The drying treatment may be usually carried out by maintaining the catalyst at a temperature of not higher than 200° C. under reduced pressure, or by flowing a drying gas such as air, nitrogen and argon through the catalyst.

The reducing treatment may be carried out by either a liquid phase reduction method or a vapor phase reduction method. However, from the viewpoint of good workability, the reducing treatment is preferably carried out by a vapor phase reduction method.

From the viewpoints of suppressing aggregation of the metal components and removing impurities contained in the precursor of the respective metal components, the temperature upon the reducing treatment is preferably not lower than room temperature, more preferably not lower than 100° C., and even more preferably not lower than 150° C., and is also preferably not higher than 500° C., more preferably not higher than 400° C., and even more preferably not higher than 350° C. The reducing treatment time may vary depending upon the reducing treatment temperature, and is preferably not less than 15 min, more preferably not less than 30 min, and even more preferably not less than 1 h, and is also preferably not more than 24 h, more preferably not more than 12 h, and even more preferably not more than 6 h.

(Specific Surface Area of Activated Carbon-Supported Metal Catalyst)

From the viewpoints of enhancing dispersibility of the metal components and improving reaction rate and yield of FDCA as well as durability of the catalyst, the specific surface area of the activated carbon-supported metal catalyst is preferably not less than 600 m²/g, more preferably not less than 700 m²/g, even more preferably not less than 800 m²/g, and further even more preferably not less than 900 m²/g, and is also preferably not more than 3000 m²/g, more preferably not more than 2500 m²/g, even more preferably not more than 2000 m²/g, and further even more preferably not more than 1500 m²/g, though it is not particularly limited thereto. Meanwhile, the specific surface area may be measured by the method described in Examples below.

<Reaction Conditions>

(Reaction Solvent)

The reaction solvent used in the production process of the present invention is not particularly limited as long as the solvent contains at least water and is capable of dissolving HMF as the raw material therein. However, from the viewpoint of satisfying both of high productivity and cost-efficiency, the solvent is preferably a polar solvent. Examples of the polar solvent include water, as well as a highly-polar aprotic organic solvent and an ionic liquid. Of these polar solvents, preferred are water, highly-polar aprotic organic solvents such as dimethylsulfoxide, dimethylacetamide, N,N-dimethylformamide, methyl isobutyl ketone, cyclohexanone, ethyl acetate, dichloromethane and N-methyl-2-pyrrolidinone, ionic liquids such as an imidazolium salt and a pyridinium salt, and the like; more preferred is at least one solvent selected from the group consisting of water, dimethylsulfoxide and an imidazolium salt; and even more preferred is water.

In the production process of the present invention, the pH of the reaction solution is not more than 7 from the viewpoint of eliminating the need of conducting additional treatments such as desalting treatment. For example, if the pH of the reaction solution initially produced is 7, as the reaction intermediate product and FDCA are produced, the pH of the reaction solution is gradually lowered and finally reaches the range of from about 0.5 to about 3.0 at the time at which the reaction is terminated.

In the production process of the present invention, the pH of the reaction solution upon charging is not more than 7, and preferably not less than 6, from the viewpoint of eliminating the need of conducting additional treatments such as desalting treatment. Also, the pH of the reaction solution upon termination of the reaction in the step (2) is preferably not more than 3 from the same viewpoint as described above, and is also preferably not less than 1, and more preferably not less than 2, from the viewpoint of enhancing yield of FDCA. Meanwhile, the pH of the reaction solution may be measured at 25° C. by the same method as described in Examples below.

(Oxygen)

The oxygen used in the production process of the present invention is not particularly limited. For example, an oxygen gas, air or a dilute gas prepared by diluting an oxygen gas or air with an inert gas such as nitrogen and argon may be used in the reaction.

The method of feeding the oxygen is not particularly limited as long as the oxygen is fed to a reaction vessel at a desired pressure and a desired flow rate. The oxygen may be flowed through a vapor phase space portion of the reaction vessel, or bubbled through the reaction solution into the vapor phase space portion of the reaction vessel. A typical oxygen feed method is such a method in which air and a diluting inert gas (such as nitrogen and argon) are mixed with each other in a known mixing apparatus to prepare a mixed gas having a well-controlled oxygen concentration, and the thus prepared mixed gas is fed to the reaction vessel at a desired flow rate.

(Reaction Method)

The reaction method used in the present invention is not particularly limited, and may be any of a batch method, a semi-continuous method and a continuous method.

In the batch method, after the HMF as the raw material and a whole amount of the catalyst are previously charged into the reaction vessel, oxygen is flowed through the reaction solution to conduct oxidation reaction of the raw material, and after completion of the reaction, the resulting reaction solution is recovered at one time.

In the semi-continuous method, for example, after a whole amount of the catalyst is charged into the reaction vessel, the oxidation reaction of the raw material is conducted while continuously feeding the raw material and oxygen into the reaction vessel, and after completion of the reaction, the resulting reaction solution is recovered at one time.

In the continuous method, the oxidation reaction of the raw material is conducted while continuously feeding all of the raw material, the catalyst and oxygen to the reaction vessel, and the resulting reaction solution is continuously recovered from the reaction vessel.

Upon the industrial practice, the continuous method and the semi-continuous method are preferred from the viewpoint of good operating efficiency.

The reaction solution is preferably stirred in order to enhance a frequency of contact of the raw material with the catalyst and oxygen. The stirring operation may be carried out using a stirring device used for ordinary reactions, such as a magnetic stirrer, a mechanical stirrer and a stirring motor equipped with an agitation blade. In the case of a large-scale process, in view of a power as needed, the stirring motor equipped with an agitation blade may be suitably used. As the stirring motor equipped with an agitation blade, there may be mentioned those stirrers equipped with an agitation blade such as a 3-bladed sweptback wing, a full-zone wing, a turbine blade and a max blend wing. It is preferred that the stirring operation is initiated before the reaction, continuously carried out during the reaction, and further continued even while cooling the reaction solution after termination of the reaction.

<Step (1)>

In the step (1) in the production process of the present invention, the oxidation reaction is conducted at a temperature of not lower than 50° C. and not higher than 110° C. until the content of the 5-hydroxymethylfurfural in the reaction solution falls within the range of not less than 0 mg/kg and not more than 1,000 mg/kg.

The content of HMF in the reaction solution is not more than 1,000 mg/kg, preferably not more than 600 mg/kg, more preferably not more than 300 mg/kg, even more preferably not more than 150 mg/kg, further even more preferably not more than 100 mg/kg, and further even more preferably not more than 80 mg/kg, from the viewpoints of suppressing occurrence of decomposition of HMF and improving yield of FDCA. The content of HMF in the reaction solution is preferably as low as possible. However, from the viewpoint of high productivity, the content of HMF in the reaction solution is preferably not less than 1 mg/kg, more preferably not less than 5 mg/kg, even more preferably not less than 10 mg/kg, further even more preferably not less than 20 mg/kg, and further even more preferably not less than 40 mg/kg.

(Reaction Temperature)

From the viewpoints of suppressing occurrence of decomposition of HMF, improving yield of FDCA and enhancing reaction rate, the temperature used upon the oxidation reaction in the step (1) is in the range of not lower than 50° C. and not higher than 110° C. More specifically, the oxidation reaction temperature in the step (1) is preferably not lower than 60° C., more preferably not lower than 70° C., even more preferably not lower than 80° C., and further even more preferably not lower than 85° C., and is also preferably not higher than 106° C., more preferably not higher than 103° C., even more preferably not higher than 100° C., and further even more preferably not higher than 95° C.

(Reaction Pressure)

From the viewpoints of improving yield of FDCA and enhancing productivity thereof, the pressure used upon the reaction in the step (1) is in the range of not less than 0.1 MPa and less than 1.0 MPa. More specifically, the reaction pressure in the step (1) is preferably not less than 0.15 MPa, more preferably not less than 0.20 MPa, and even more preferably not less than 0.25 MPa, and is also preferably not more than 0.8 MPa, more preferably not more than 0.6 MPa, even more preferably not more than 0.4 MPa, and further even more preferably not more than 0.3 MPa.

(Oxygen Feed Amount)

The amount of the oxygen fed until the time at which the step (1) is terminated is preferably not less than 85 mol %, more preferably not less than 90 mol %, even more preferably not less than 93 mol %, further even more preferably not less than 96 mol %, and further even more preferably not less than 100 mol %, and is also preferably not more than 120 mol %, more preferably less than 120 mol %, even more preferably not more than 110 mol %, further even more preferably not more than 108 mol %, and further even more preferably not more than 105 mol %, on the basis of HMF charged, from the viewpoint of improving yield of FDCA.

Meanwhile, it is preferred that before being heated in the step (1), oxygen is previously added to HMF charged. The amount of the oxygen added is not particularly limited, and is preferably not less than 5 mol %, more preferably not less than 15 mol %, even more preferably not less than 30 mol %, and further even more preferably not less than 35 mol %, and is also preferably not more than 60 mol %, more preferably not more than 50 mol %, even more preferably not more than 45 mol %, and further even more preferably not more than 40 mol %, on the basis of HMF charged, from the viewpoints of improving yield of FDCA and suppressing occurrence of a decomposition reaction thereof.

The amount of the oxygen fed in the step (1) is preferably not less than 40 mol %, more preferably not less than 50 mol %, even more preferably not less than 60 mol %, and further even more preferably not less than 65 mol %, and is also preferably not more than 100 mol %, more preferably not more than 90 mol %, even more preferably not more than 80 mol %, and further even more preferably not more than 70 mol %, on the basis of HMF charged, from the viewpoint of improving yield of FDCA.

(Oxygen Flow Rate)

The flow rate of the oxygen in the step (1) is preferably not less than 5 mol %/h, more preferably not less than 10 mol %/h, even more preferably not less than 15 mol %/h, and further even more preferably not less than 20 mol %/h, and is also preferably not more than 50 mol %/h, more preferably not more than 40 mol %/h, even more preferably not more than 30 mol %/h, and further even more preferably not more than 25 mol %/h, on the basis of HMF charged, from the viewpoints of improving yield of FDCA and suppressing occurrence of a decomposition reaction thereof.

<Step (2)>

In the step (2) in the production process of the present invention, the reaction solution obtained after completion of the step (1) is subjected to the oxidation reaction at a temperature of not lower than 140° C. and not higher than 250° C.

(Reaction Temperature)

From the viewpoints of enhancing solubility of FDCA to improve productivity thereof, and satisfying both of suppressing the decomposition reaction and promoting the oxidation reaction, the temperature used upon the oxidation reaction in the step (2) is in the range of not lower than 140° C. and not higher than 250° C. More specifically, the oxidation reaction temperature in the step (2) is preferably not lower than 145° C., more preferably not lower than 150° C., even more preferably not lower than 155° C., and further even more preferably not lower than 160° C., and is also preferably not higher than 250° C., more preferably not higher than 220° C., even more preferably not higher than 190° C., further even more preferably not higher than 180° C., and further even more preferably not higher than 170° C.

(Reaction Pressure)

From the viewpoints of improving yield and productivity of FDCA, the pressure used upon the reaction in the step (2) is in the range of not less than 0.1 MPa and less than 1.0 MPa. More specifically, the reaction pressure in the step (2) is preferably not less than 0.2 MPa, more preferably not less than 0.4 MPa, even more preferably not less than 0.6 MPa, further even more preferably not less than 0.7 MPa, further even more preferably not less than 0.8 MPa, and further even more preferably not less than 0.85 MPa, and is also preferably not more than 0.98 MPa, more preferably not more than 0.96 MPa, even more preferably not more than 0.94 MPa, and further even more preferably not more than 0.92 MPa.

(Oxygen Feed Amount)

The amount of the oxygen fed until the time at which the step (2) is terminated is not less than 120 mol %, preferably not less than 124 mol %, more preferably not less than 127 mol %, and even more preferably not less than 130 mol %, and is also not more than 140 mol %, preferably not more than 138 mol %, more preferably not more than 136 mol %, and even more preferably not more than 135 mol %, on the basis of HMF charged, from the viewpoints of improving yield of FDCA and suppressing occurrence of a decomposition reaction thereof.

The amount of the oxygen fed in the step (2) is preferably not less than 15 mol %, more preferably not less than 20 mol %, and even more preferably not less than 25 mol %, on the basis of HMF charged, from the viewpoint of improving yield of FDCA, and is also preferably not more than 50 mol %, more preferably not more than 45 mol %, and even more preferably not more than 42 mol %, on the basis of HMF charged, from the viewpoint of suppressing occurrence of a decomposition reaction of FDCA.

(Oxygen Flow Rate)

The flow rate of the oxygen in the step (2) is preferably not less than 5 mol %/h, more preferably not less than 10 mol %/h, even more preferably not less than 15 mol %/h, further even more preferably not less than 20 mol %/h, and further even more preferably not less than 24 mol %/h, and is also preferably not more than 60 mol %/h, more preferably not more than 55 mol %/h, even more preferably not more than 50 mol %/h, and further even more preferably not more than 45 mol %/h, on the basis of HMF charged, from the viewpoints of improving yield of FDCA and suppressing occurrence of a decomposition reaction thereof.

(Refining)

In the production process of the present invention, from the viewpoint of increasing purity of the resulting product, FDCA obtained after completion of the oxidation reaction may be subjected to refining treatment by conventionally known methods as described in JP 2001-288139A, etc. For example, a water-containing liquid is added to the oxide of HMF obtained by filtration after completion of the oxidation reaction, followed by cooling the resulting mixture to prepare a slurry. The thus prepared slurry is dissolved under heating, and then subjected to hydrogenation treatment in the presence of a hydrogenation catalyst while being kept in the dissolved state. The resulting reaction product may be subjected to crystallization and solid-liquid separation to thereby refine the reaction product. It is preferred that the solid obtained by solid-liquid separation after completion of the refining step is directly dried to thereby produce a final product. Furthermore, after adding an amount of fresh water to the product, the resulting mixture may be subjected to solid-liquid separation, and then the obtained solid may be dried to produce a final product.

With respect to the aforementioned embodiments, the present invention further provides the following aspects relating to the process for producing 2,5-furan dicarboxylic acid.

<1> A process for producing 2,5-furan dicarboxylic acid by subjecting 5-hydroxymethylfurfural to oxidation reaction in the presence of water, oxygen and an activated carbon-supported metal catalyst containing a noble metal, the process including the following steps (1) and (2) in which the steps (1) and (2) are carried out under a pressure of not less than 0.1 MPa and less than 1.0 MPa while maintaining a reaction solution at a pH of not more than 7, and an amount of the oxygen fed until a time at which the step (2) is terminated is not less than 120 mol % and not more than 140 mol % on the basis of the 5-hydroxymethylfurfural charged:

step (1): conducting the oxidation reaction at a temperature of not lower than 50° C. and not higher than 110° C. until a content of the 5-hydroxymethylfurfural in the reaction solution falls within the range of not less than 0 mg/kg and not more than 1,000 mg/kg; and step (2): subjecting the reaction solution obtained after completion of the step (1) to the oxidation reaction at a temperature of not lower than 140° C. and not higher than 250° C.

<2> The process for producing 2,5-furan dicarboxylic acid according to the aspect <1>, wherein the noble metal is at least one metal selected from the group consisting of platinum group metals.

<3> The process for producing 2,5-furan dicarboxylic acid according to the aspect <1> or <2>, wherein the noble metal is platinum.

<4> The process for producing 2,5-furan dicarboxylic acid according to any one of the aspects <1> to <3>, wherein the activated carbon-supported metal catalyst further includes at least one metal (A) selected from the group consisting of bismuth and tin.

<5> The process for producing 2,5-furan dicarboxylic acid according to any one of the aspects <1> to <4>, wherein a mass ratio of the noble metal to the metal (A) [noble metal/metal (A)] in the catalyst is preferably not less than 1, more preferably not less than 2, even more preferably not less than 3, and further even more preferably not less than 4, and is also preferably not more than 10, more preferably not more than 9, even more preferably not more than 8, further even more preferably not more than 7, and further even more preferably not more than 6.

<6> The process for producing 2,5-furan dicarboxylic acid according to any one of the aspects <1> to <5>, wherein a specific surface area of the activated carbon is preferably not less than 600 m$^2$/g, more preferably not less than 700 m$^2$/g, even more preferably not less than 800 m$^2$/g, and further even more preferably not less than 900 m$^2$/g, and is also preferably not more than 3000 m$^2$/g, more preferably not more than 2500 m$^2$/g, even more preferably not more than 2000 m$^2$/g, and further even more preferably not more than 1500 m$^2$/g.

<7> The process for producing 2,5-furan dicarboxylic acid according to any one of the aspects <1> to <6>, wherein a specific surface area of the activated carbon-supported metal catalyst is preferably not less than 600 m$^2$/g, more preferably not less than 700 m$^2$/g, even more preferably not less than 800 m$^2$/g, and further even more preferably not less than 900 m$^2$/g, and is also preferably not more than 3000 m$^2$/g, more preferably not more than 2500 m$^2$/g, even more preferably not more than 2000 m$^2$/g, and further even more preferably not more than 1500 m$^2$/g.

<8> The process for producing 2,5-furan dicarboxylic acid according to any one of the aspects <1> to <7>, wherein an amount of the noble metal supported on the activated carbon-supported metal catalyst is preferably not less than 0.5% by mass, more preferably not less than 1% by mass, even more preferably not less than 2% by mass, and further even more preferably not less than 3% by mass, and is also preferably not more than 15% by mass, more preferably not more than 10% by mass, even more preferably not more than 8% by mass, and further even more preferably not more than 7% by mass, on the basis of a whole amount of the catalyst.

<9> The process for producing 2,5-furan dicarboxylic acid according to any one of the aspects <1> to <8>, wherein an amount of the activated carbon-supported metal catalyst used is controlled such that a mass of the noble metal used in the catalyst is preferably not less than 0.5% by mass, more preferably not less than 1% by mass, even more preferably not less than 2% by mass, and further even more preferably not less than 3% by mass, and is also preferably not more than 10% by mass, more preferably not more than 9% by mass, even more preferably not more than 8% by mass, and further even more preferably not more than 7% by mass, on the basis of a mass of HMF.

<10> The process for producing 2,5-furan dicarboxylic acid according to any one of the aspects <1> to <9>, wherein a reaction solvent used in the process is a solvent capable of dissolving HMF as the raw material therein, the reaction solvent being preferably at least one solvent selected from the group consisting of polar solvents such as water, a highly-polar aprotonic organic solvent and an ionic liquid, more preferably at least one solvent selected from the group consisting of water, dimethylsulfoxide, dimethylacetamide, N,N-dimethylformamide, methyl isobutyl ketone, cyclohexanone, ethyl acetate, dichloromethane, N-methyl-2-pyrrolidinone, an imidazolium salt and a pyridinium salt, even more preferably at least one solvent selected from the group consisting of water, dimethylsulfoxide and an imidazolium salt, and further even more preferably water.

<11> The process for producing 2,5-furan dicarboxylic acid according to any one of the aspects <1> to <10>, wherein a content of HMF in a whole amount of the reaction solution upon initiation of the reaction in the step (1) is preferably not less than 0.5% by mass, more preferably not less than 1.0% by mass, even more preferably not less than 2.0% by mass, and further even more preferably not less than 3.0% by mass, and is also preferably not more than 8.0% by mass, more preferably not more than 7.0% by mass, even more preferably not more than 6.0% by mass, and further even more preferably not more than 5.0% by mass.

<12> The process for producing 2,5-furan dicarboxylic acid according to any one of the aspects <1> to <11>, wherein in the step (1), the oxidation reaction is conducted until a content of HMF in the reaction solution preferably falls within the range of not more than 600 mg/kg, more preferably not more than 300 mg/kg, even more preferably not more than 150 mg/kg, further even more preferably not more than 100 mg/kg, and further even more preferably not more than 80 mg/kg, and also until a content of HMF in the reaction solution preferably falls within the range of not less than 1 mg/kg, more preferably not less than 5 mg/kg, even more preferably not less than 10 mg/kg, further even more preferably not less than 20 mg/kg, and further even more preferably not less than 40 mg/kg.

<13> The process for producing 2,5-furan dicarboxylic acid according to any one of the aspects <1> to <12>, wherein a temperature of the oxidation reaction in the step (1) is preferably not lower than 60° C., more preferably not lower than 70° C., even more preferably not lower than 80° C., and further even more preferably not lower than 85° C., and is also preferably not higher than 106° C., more preferably not higher than 103° C., even more preferably not higher than 100° C., and further even more preferably not higher than 95° C.
<14> The process for producing 2,5-furan dicarboxylic acid according to any one of the aspects <1> to <13>, wherein a pressure of the reaction in the step (1) is preferably not less than 0.15 MPa, more preferably not less than 0.20 MPa, and even more preferably not less than 0.25 MPa, and is also preferably not more than 0.8 MPa, more preferably not more than 0.6 MPa, even more preferably not more than 0.4 MPa, and further even more preferably not more than 0.3 MPa.
<15> The process for producing 2,5-furan dicarboxylic acid according to any one of the aspects <1> to <14>, wherein an amount of the oxygen fed until the time at which the step (1) is terminated is preferably not less than 85 mol %, more preferably not less than 90 mol %, even more preferably not less than 93 mol %, further even more preferably not less than 96 mol %, and further even more preferably not less than 100 mol %, and is also preferably not more than 120 mol %, more preferably less than 120 mol %, even more preferably not more than 110 mol %, further even more preferably not more than 108 mol %, and further even more preferably not more than 105 mol %, on the basis of HMF charged.
<16> The process for producing 2,5-furan dicarboxylic acid according to any one of the aspects <1> to <15>, wherein an amount of the oxygen previously added before being heated in the step (1) is preferably not less than 5 mol %, more preferably not less than 15 mol %, even more preferably not less than 30 mol %, and further even more preferably not less than 35 mol %, and is also preferably not more than 60 mol %, more preferably not more than 50 mol %, even more preferably not more than 45 mol %, and further even more preferably not more than 40 mol %, on the basis of HMF charged.
<17> The process for producing 2,5-furan dicarboxylic acid according to any one of the aspects <1> to <16>, wherein a flow rate of the oxygen in the step (1) is preferably not less than 5 mol %/h, more preferably not less than 10 mol %/h, even more preferably not less than 15 mol %/h, and further even more preferably not less than 20 mol %/h, and is also preferably not more than 50 mol %/h, more preferably not more than 40 mol %/h, even more preferably not more than 30 mol %/h, and further even more preferably not more than 25 mol %/h, on the basis of HMF charged.
<18> The process for producing 2,5-furan dicarboxylic acid according to any one of the aspects <1> to <17>, wherein a temperature of the oxidation reaction in the step (2) is preferably not lower than 145° C., more preferably not lower than 150° C., even more preferably not lower than 155° C., and further even more preferably not lower than 160° C., and is also preferably not higher than 250° C., more preferably not higher than 220° C., even more preferably not higher than 190° C., further even more preferably not higher than 180° C., and further even more preferably not higher than 170° C.
<19> The process for producing 2,5-furan dicarboxylic acid according to any one of the aspects <1> to <18>, wherein a pressure of the reaction in the step (2) is preferably not less than 0.2 MPa, more preferably not less than 0.4 MPa, even more preferably not less than 0.6 MPa, further even more preferably not less than 0.7 MPa, further even more preferably not less than 0.8 MPa, and further even more preferably not less than 0.85 MPa, and is also preferably not more than 0.98 MPa, more preferably not more than 0.96 MPa, even more preferably not more than 0.94 MPa, and further even more preferably not more than 0.92 MPa.
<20> The process for producing 2,5-furan dicarboxylic acid according to any one of the aspects <1> to <19>, wherein an amount of the oxygen fed until the time at which the step (2) is terminated is preferably not less than 124 mol %, more preferably not less than 127 mol %, and even more preferably not less than 130 mol %, and is also preferably not more than 138 mol %, more preferably not more than 136 mol %, and even more preferably not more than 135 mol %, on the basis of HMF charged.
<21> The process for producing 2,5-furan dicarboxylic acid according to any one of the aspects <1> to <20>, wherein an amount of the oxygen fed in the step (2) is preferably not less than 15 mol %, more preferably not less than 20 mol %, and even more preferably not less than 25 mol %, and is also preferably not more than 50 mol %, more preferably not more than 45 mol %, and even more preferably not more than 42 mol %, on the basis of HMF charged.
<22> The process for producing 2,5-furan dicarboxylic acid according to any one of the aspects <1> to <21>, wherein a flow rate of the oxygen in the step (2) is preferably not less than 5 mol %/h, more preferably not less than 10 mol %/h, even more preferably not less than 15 mol %/h, further even more preferably not less than 20 mol %/h, and further even more preferably not less than 24 mol %/h, and is also preferably not more than 60 mol %/h, more preferably not more than mol %/h, even more preferably not more than 50 mol %/h, and further even more preferably not more than 45 mol %/h, on the basis of HMF charged.
<23> The process for producing 2,5-furan dicarboxylic acid according to any one of the aspects <1> to <22>, wherein a reaction method used in the process is preferably any of a batch method, a semi-continuous method and a continuous method, and more preferably a continuous method or a semi-continuous method.
<24> The process for producing 2,5-furan dicarboxylic acid according to any one of the aspects <1> to <23>, wherein a pH of the reaction solution upon initiation of the reaction in the step (1) is preferably not less than 6.
<25> The process for producing 2,5-furan dicarboxylic acid according to any one of the aspects <1> to <24>, wherein a pH of the reaction solution upon termination of the reaction in the step (2) is preferably not more than 3, and is also preferably not less than 1, and more preferably not less than 2.

EXAMPLES

In the following Examples and Comparative Examples, the term "%" means "% by mass" unless otherwise specified.

Meanwhile, the respective properties, etc., were measured by the following methods.
(1) Conversion Rate of HMF and Yield of FDCA Using a high-performance liquid chromatograph available from Shimadzu Corporation, amounts of HMF and FDCA were measured under the following conditions, and the conversion rate (mol %) of HMF and the yield (mol %) of FDCA were calculated from a ratio of the thus measured amount of HMF relative to a molar amount of HMF as the raw material and a ratio of the thus measured amount of FDCA relative to the molar amount of HMF as the raw material, respectively.

<Conditions for Measuring Amount of HMF>
Detector: RI detector
Column: "ICSep COREGEL-87H"
Temperature: 80° C.
Eluent: 0.1% Trifluoroacetic acid-containing water
Flow rate: 0.6 mL/min
Diluting solvent for sample to be measured: Ultrapure water <Conditions for Measurement of Amount of FDCA>
Detector: UV detector (254 nm)
Column: "L-column2 ODS" available from Kanto Chemical Co., Inc.
Temperature: 40° C.
Eluent: Mixed solution prepared by mixing 0.1% trifluoroacetic acid-containing ultrapure water and 0.1% trifluoroacetic acid-containing methanol "HPLC grade" available from Wako Pure Chemical Industries, Ltd., at a volume ratio of 1/1
Flow rate: 1.0 mL/min
Diluting solvent for sample to be measured: Dimethylsulfoxide available from Wako Pure Chemical Industries, Ltd.

(2) BET Specific Surface Area of Activated Carbon-Supported Metal Catalyst

Using a BET specific surface area measuring apparatus "Micromeritics FlowSorb III" available from Shimadzu Corporation, the BET specific surface area of the activated carbon-supported metal catalyst was measured under the following conditions.
Among of sample: 0.1 g
Deaeration conditions: 120° C., 10 min
Adsorbing gas: Nitrogen gas (3) Among of Platinum (Pt) Eluted A sample was weighed in an amount of 0.5 g in a microwave-dedicated glass vessel, and then sulfuric acid, nitric aid and hydrogen peroxide were charged into the glass vessel. The contents of the glass vessel were subjected to microwave digestion using a "STAR Microwave Digestion System" available from CEM Corporation. Next, the resulting reaction solution was cooled to room temperature and then transferred into a flask using pure water, and thereafter pure water was added to the reaction solution until a total volume thereof reached 50 mL. The amount of platinum contained in the thus obtained reaction solution was measured under the following conditions using a "Optima 5300DV multichannel ICP emission spectroscopic analyzer" available from Perkin-Elmer Corporation to calculate an amount of platinum eluted out from the platinum in the supported catalyst used.

<Conditions for Measuring Amount of Pt>
Plasma output: 1300 W
Plasma gas: 15 L/min
Auxiliary gas: 1 L/min
Sheath gas: 0.7 L/min
Pump flow rate: 1 mL/min (4) pH A pH controller was connected with a glass electrode and a temperature-compensating temperature sensing element. The glass electrode and the temperature-compensating temperature sensing element were dipped in a measuring solution at room temperature (25° C.), and after the elapse of 10 min, the indicated value of the pH meter was read out. Next, the glass electrode was fully rinsed with water, and then dipped again in the same measuring solution after wiping off water therefrom, and after the elapse of 10 min, the indicated value of the pH meter was read out. The above procedure was repeated three times to calculate an average value of the thus measured values.

pH Controller: "Model FD-02" available from FINE
Glass electrode: "Model HOR6367" available from HORIBA Ltd.
Temperature-compensating temperature sensing element: "Model NT-220" available from TGK Co., Ltd.
Concentration of measuring solution: 15 mmol/L
Diluting solvent for sample to be measured: Ultrapure water Example 1

(1) Charging of Raw Material, etc.

A 1 L-capacity titanium autoclave available from Nitto Koatsu Co., Ltd., was charged with 10.04 g of HMF (available from Sigma-Aldrich; purity: 95.9%) as a raw material, 10.00 g of an activated carbon-supported metal catalyst (available from Evonik Industries AG; water content: 51.0%: specific surface area: 987 $m^2/g$) on which 5% of Pt and 1% of Bi were supported, and 228.66 g of ion-exchanged water as a reaction solvent. The autoclave was hermetically closed, and then an inside atmosphere of the autoclave was fully replaced with nitrogen while stirring the contents thereof. Thereafter, the autoclave was opened, and nitrogen was flowed therethrough at a rate of 50 mL/min. Next, after the inside atmosphere of the autoclave was fully replaced with oxygen, the autoclave was hermetically closed, and oxygen in an amount of 37 mol % (based on HMF charged) was injected thereinto. Meanwhile, the pH of the reaction solution at an initial stage of the reaction was 6.7, and the gauge pressure upon the reaction was 0.2 MPa.

(2) Step (1)

Next, the resulting reaction solution was heated to 90° C. over 23 min. After the temperature of 90° C. was reached, the reaction solution was reacted for 3 h while feeding oxygen thereto at a rate of 21.9 mol %/h. The thus obtained reaction mixed solution was mixed with a predetermined amount of dimethylsulfoxide. The resulting mixture was subjected to ultrasonic treatment for 10 min, and then subjected to filtration using a PTFE membrane filter having a pore diameter of 0.2 μm to separate the catalyst therefrom, thereby obtaining a filtrate. The resulting filtrate was sampled, and the amount of HMF contained therein was measured under the aforementioned measuring conditions to calculate a content (mg/kg) of HMF in the reaction solution upon termination of the reaction. The results are shown in Table 1. In addition, the resulting reaction mixed solution was subjected to filtration using a PTFE membrane filter having a pore diameter of 0.2 μm to separate the activated carbon-supported metal catalyst therefrom, thereby obtaining a filtrate. The pH of the reaction solution obtained upon termination of the reaction was 2.1.

(3) Step (2)

After completion of the step (1), the flow rate of the oxygen was changed to 27.8 mol %/h, and the reaction solution was heated to 165° C. over 47 min. Next, after the elapse of 13 min, the reaction was terminated, and the obtained reaction solution was cooled while stirring until the temperature of the contents of the autoclave was reduced to 30° C. or lower.

(4) Additional Treatment

The reaction mixed solution obtained in the above item (3) was subjected to filtration using a PTFE membrane filter having a pore diameter of 0.2 μm to separate the activated carbon-supported metal catalyst therefrom, thereby obtaining a filtrate. The activated carbon-supported metal catalyst thus separated by filtration was mixed with a predetermined amount of dimethylsulfoxide. The resulting mixture was subjected to ultrasonic treatment for 10 min, and then subjected again to filtration using a PTFE membrane filter having a pore diameter of 0.2 μm, thereby obtaining a catalyst wash solution.

(5) Analysis of Reaction Product

The pH of the thus obtained filtrate was 2.5. The resulting filtrate and catalyst wash solution were sampled and subjected to liquid chromatography to measure the conversion rate of HMF and the yield of FDCA.

In addition, the filtrate was subjected to vacuum freeze drying to distil off the solvent therefrom. The obtained solid sample was pretreated and subjected to emission spectrometry using an ICP emission spectroscopic analyzer to measure an amount of Pt eluted therefrom and calculate a ratio (% by mass) of Pt eluted per an amount of Pt supported on the catalyst used. The results are shown in Table 1.

Examples 2 to 6

The oxidation reaction, the additional treatment and the analysis of the reaction product were carried out under the same conditions as in Example 1 except that the reaction conditions were changed to those shown in Table 1. The results are shown in Table 1.

Example 7

The oxidation reaction, the additional treatment and the analysis of the reaction product were carried out under the same conditions as in Example 1 except that the autoclave was replaced with a 1 L Hastelloy ("ALLOY C-276") autoclave (available from Taiatsu Techno Corporation), and the reaction conditions were changed to those shown in Table 1. The results are shown in Table 1.

Examples 8 to 10

The oxidation reaction, the additional treatment and the analysis of the reaction product were carried out under the same conditions as in Example 7 except that the reaction conditions were changed to those shown in Table 1. The results are shown in Table 1.

Comparative Examples 1 and 2

The oxidation reaction, the additional treatment and the analysis of the reaction product were carried out under the same conditions as in Example 1 except that upon charging the raw material, the reaction conditions of the step (1) were changed to those shown in Table 1, and no step (2) was conducted. The results are shown in Table 1.

Comparative Example 3

(1) Charging of Raw Material, etc.

A 1 L-capacity titanium autoclave available from Nitto Koatsu Co., Ltd., was charged with 12.51 g of HMF (available from Sigma-Aldrich; purity: 95.9%) as a raw material, 15.05 g of an activated carbon-supported metal catalyst (available from Evonik Industries AG; water content: 59.6%: specific surface area: 890 $m^2/g$) on which 5% of Pt and 1% of Bi were supported, and 282.60 g of ion-exchanged water as a reaction solvent. The autoclave was hermetically closed, and then an inside atmosphere of the autoclave was fully replaced with nitrogen while stirring the contents thereof. Thereafter, the autoclave was opened, and nitrogen was flowed therethrough at a rate of 20 mL/min. Next, after the inside atmosphere of the autoclave was fully replaced with oxygen, the autoclave was hermetically closed, and oxygen in an amount of 38 mol % (based on HMF charged) was injected thereinto. Meanwhile, the pH of the reaction solution at an initial stage of the reaction was 6.7, and the gauge pressure upon the reaction was 0.2 MPa.

Subsequently, the oxidation reaction, the additional treatment and the analysis of the reaction product were carried out under the same conditions as in Example 1 except that the reaction conditions of the step (1) and the step (2) were respectively changed to those shown in Table 1. The results are shown in Table 1.

Comparative Example 4

The oxidation reaction, the additional treatment and the analysis of the reaction product were carried out under the same conditions as in Comparative Example 3 except that the reaction conditions were changed to those shown in Table 1. The results are shown in Table 1.

Comparative Examples 5 to 7

The oxidation reaction, the additional treatment and the analysis of the reaction products were carried out under the same conditions as in Example 1 except that the reaction condition were changed to those shown in Table 1.

The results are shown in Table 1.

Comparative Example 8

The oxidation reaction, the additional treatment and the analysis of the reaction product were carried out under the same conditions as in Example 1 except that the catalyst was replaced with a supported metal catalyst (available from N.E. Chemcat Corporation; water content: 0.0%; specific surface area: 56 $m^2/g$) prepared by supporting 5% of Pt on zirconium dioxide (ZrO2), and the reaction conditions were changed to those shown in Table 1. The results are shown in Table 1.

Comparative Examples 9 to 11

The oxidation reaction, the additional treatment and the analysis of the reaction product were carried out under the same conditions as in Example 7 except that the reaction conditions were changed to those shown in Table 1. The results are shown in Table 1.

TABLE 1

|  | Examples | | | | |
| --- | --- | --- | --- | --- | --- |
|  | 1 | 2 | 3 | 4 | 5 |
| Amount of oxygen added before heating in step (1) (mol %) | 37 | 38 | 38 | 36 | 37 |
| Step (1) | | | | | |
| Heating time (min) | 23 | 22 | 21 | 23 | 19 |
| Pressure upon reaction (MPa) | 0.2 | 0.2 | 0.2 | 0.2 | 0.2 |
| Reaction temperature (° C.) | 90 | 90 | 90 | 90 | 70 |
| Reaction time (h) | 3.0 | 3.0 | 3.0 | 3.0 | 5.0 |
| Oxygen flow rate (mol %/h)[*1] | 21.9 | 22.0 | 22.1 | 21.7 | 12.6 |
| Amount of oxygen fed until the time at which step (1) was terminated (mol %)[*2] | 103 | 104 | 104 | 101 | 100 |
| Content of HMF in reaction solution upon termination of step (1) (mg/kg) | 48 | 49 | 130 | 94 | 72 |
| Step (2) | | | | | |
| Heating time (min) | 47 | 27 | 40 | 40 | 43 |
| Pressure upon reaction (MPa) | 0.9 | 0.9 | 0.9 | 0.9 | 0.9 |
| Reaction temperature (° C.) | 165 | 155 | 175 | 175 | 175 |
| Reaction time (h) | 1.0 | 2.0 | 0.75 | 0.75 | 0.75 |
| Oxygen flow rate (mol %/h)[*1] | 27.8 | 25.3 | 30.8 | 41.1 | 32.1 |
| Amount of oxygen fed until the time at which step (2) was terminated (mol %)[*2] | 131 | 134 | 127 | 131 | 124 |
| Conversion rate of HMF (%) | 100 | 100 | 100 | 100 | 100 |
| Yield of FDCA (%) | 94.8 | 93.6 | 91.5 | 91.1 | 92.0 |
| Amount of Pt eluted (% by mass)[*3] | 0.0187 | 0.0058 | 0.0224 | 0.0166 | 0.0038 |
| pH after separation by filtration | 2.5 | 2.4 | 2.3 | 2.4 | 2.3 |

|  | Examples | | | | |
| --- | --- | --- | --- | --- | --- |
|  | 6 | 7 | 8 | 9 | 10 |
| Amount of oxygen added before heating in step (1) (mol %) | 35 | 35 | 10 | 47 | 38 |
| Step (1) | | | | | |
| Heating time (min) | 18 | 14 | 17 | 14 | 28 |
| Pressure upon reaction (MPa) | 0.2 | 0.1 | 0.1 | 0.1 | 0.1 |
| Reaction temperature (° C.) | 70 | 90 | 90 | 90 | 90 |
| Reaction time (h) | 5.0 | 3.0 | 3.0 | 5.5 | 1.6 |
| Oxygen flow rate (mol %/h)[*1] | 12.6 | 20.4 | 31.4 | 9.7 | 44.0 |
| Amount of oxygen fed until the time at which step (1) was terminated (mol %)[*2] | 98 | 96 | 104 | 100 | 108 |
| Content of HMF in reaction solution upon termination of step (1) (mg/kg) | 82 | 839 | 34 | 8 | 224 |
| Step (2) | | | | | |
| Heating time (min) | 44 | 26 | 30 | 24 | 31 |
| Pressure upon reaction (MPa) | 0.7 | 0.7 | 0.7 | 0.7 | 0.7 |
| Reaction temperature (° C.) | 155 | 165 | 165 | 165 | 165 |
| Reaction time (h) | 1.5 | 1.0 | 1.0 | 1.0 | 1.0 |
| Oxygen flow rate (mol %/h)[*1] | 7.3 | 41.1 | 34.0 | 32.9 | 32.4 |
| Amount of oxygen fed until the time at which step (2) was terminated (mol %)[*2] | 130 | 137 | 138 | 133 | 140 |
| Conversion rate of HMF (%) | 100 | 100 | 100 | 100 | 100 |
| Yield of FDCA (%) | 90.6 | 94.4 | 89.1 | 90.9 | 94.0 |
| Amount of Pt eluted (% by mass)[*3] | 0.0136 | 0.0031 | 0.0089 | 0.0223 | 0.0271 |
| pH after separation by filtration | 2.3 | 2.5 | 2.4 | 2.4 | 2.4 |

|  | Comparative Examples | | | | | |
| --- | --- | --- | --- | --- | --- | --- |
|  | 1 | 2 | 3 | 4 | 5 | 6 |
| Amount of oxygen added before heating in step (1) (mol %) | 123 | 128 | 38 | 38 | 6 | 42 |
| Step (1) | | | | | | |
| Heating time (min) | 25 | 63 | 24 | 28 | 20 | 20 |
| Pressure upon reaction (MPa) | 0.9 | 0.9 | 0.2 | 0.2 | 0.2 | 0.2 |

TABLE 1-continued

| | | | | | | |
|---|---|---|---|---|---|---|
| Reaction temperature (° C.) | 90 | 165 | 90 | 90 | 90 | 90 |
| Reaction time (h) | 3.0 | 3 | 3.0 | 3.0 | 3.0 | 3.0 |
| Oxygen flow rate (mol %/h)*[1] | 28.6 | 14.0 | 18.3 | 17.9 | 22.9 | 24.6 |
| Amount of oxygen fed until the time at which step (1) was terminated (mol %)*[2] | 209 | 170 | 93 | 91 | 76 | 116 |
| Content of HMF in reaction solution upon termination of step (1) (mg/kg) | — | — | 10937 | 5660 | 1543 | 99 |
| Step (2) | | | | | | |
| Heating time (min) | — | — | 50 | 65 | 39 | 39 |
| Pressure upon reaction (MPa) | — | — | 0.9 | 0.9 | 6.9 | 0.9 |
| Reaction temperature (° C.) | — | — | 165 | 165 | 165 | 165 |
| Reaction time (h) | — | — | 4.0 | 5.0 | 1.5 | 1.5 |
| Oxygen flow rate (mol %/h)*[1] | — | — | 0 | 10.2 | 21.3 | 21.3 |
| Amount of oxygen fed until the time at which step (2) was terminated (mol %)*[2] | — | — | 93 | 142 | 108 | 148 |
| Conversion rate of HMF (%) | 100 | 100 | 100 | 99.9 | 100 | 100 |
| Yield of FDCA (%) | 66.4 | 71.3 | 41.0 | 45.5 | 44.6 | 76.9 |
| Amount of Pt eluted (% by mass)*[3] | 0.0004 | 0.0002 | 0.0125 | 0.0344 | 0.0151 | 0.0029 |
| pH after separation by filtration | 2.4 | 2.5 | 2.1 | 2.6 | 2.9 | 2.4 |

| | Comparative Examples | | | | |
|---|---|---|---|---|---|
| | 7 | 8 | 9 | 10 | 11 |
| Amount of oxygen added before heating in step (1) (mol %) | 35 | 40 | 35 | 36 | 38 |
| Step (1) | | | | | |
| Heating time (min) | 20 | 24 | 11 | 18 | 15 |
| Pressure upon reaction (MPa) | 0.2 | 0.3 | 0.2 | 0.2 | 0.2 |
| Reaction temperature (° C.) | 90 | 90 | 40 | 90 | 90 |
| Reaction time (h) | 3.0 | 7.0 | 3.0 | 3.0 | 3.0 |
| Oxygen flow rate (mol %/h)*[1] | 25.8 | 12.6 | 22.2 | 22.5 | 18.3 |
| Amount of oxygen fed until the time at which step (1) was terminated (mol %)*[2] | 112 | 129 | 101 | 104 | 93 |
| Content of HMF in reaction solution upon termination of step (1) (mg/kg) | 12 | 9983 | 12993 | 20 | 1910 |
| Step (2) | | | | | |
| Heating time (min) | 36 | 41 | 29 | 12 | 19 |
| Pressure upon reaction (MPa) | 0.7 | 0.9 | 0.7 | 0.7 | 0.7 |
| Reaction temperature (° C.) | 165 | 165 | 165 | 120 | 165 |
| Reaction time (h) | 1.5 | 1.5 | 1.0 | 1.0 | 3.0 |
| Oxygen flow rate (mol %/h)*[1] | 0.0 | 8.6 | 33.5 | 30.5 | 11.9 |
| Amount of oxygen fed until the time at which step (2) was terminated (mol %)*[2] | 112 | 141 | 135 | 134 | 129 |
| Conversion rate of HMF (%) | 100 | 98.4 | 100 | 100 | 100 |
| Yield of FDCA (%) | 73.1 | 7.3 | 60.9 | 74.0 | 67.5 |
| Amount of Pt eluted (% by mass)*[3] | 0.0185 | 0.0483 | 0.0126 | 0.0005 | 0.0052 |
| pH after separation by filtration | 2.4 | 2.5 | 2.5 | 2.4 | 2.2 |

Note
*[1]Flow rate of oxygen on the basis of HMF as raw material
*[2]Amount of oxygen fed on the basis of HMF as raw material
*[3]Ratio of amount of Pt eluted to amount of Pt supported on catalyst used [amount of Pt eluted/amount of Pt supported on catalyst used]

As recognized from the results of the aforementioned Examples and Comparative Examples, according to the present invention, it is possible to obtain FDCA with high yield, to produce FDCA with high productivity in an industrially useful manner.

INDUSTRIAL APPLICABILITY 2,5-Furan dicarboxylic acid obtained by the production process of the present invention is useful as monomers for synthetic resins or toner binders as well as intermediate products for medicines, agricultural chemicals, insecticides, antibacterial agents, perfumes and other products in various applications.

The invention claimed is:

1. A process for producing 2,5-furan dicarboxylic acid by subjecting 5-hydroxymethylfurfural to oxidation reaction in the presence of water, oxygen and an activated carbon-supported metal catalyst comprising a noble metal, the process comprising the following steps (1) and (2) in which the steps (1) and (2) are carried out under a pressure of not less than 0.1 MPa and less than 1.0 MPa while maintaining a reaction solution at a pH of not more than 7, and an amount of the oxygen fed until a time at which the step (2) is terminated is not less than 120 mol % and not more than 140 mol % on the basis of the 5-hydroxymethylfurfural charged:

step (1): conducting the oxidation reaction at a temperature of not lower than 50° C. and not higher than 110° C. until a content of the 5-hydroxymethylfurfural in the reaction solution falls within the range of not less than 0 mg/kg and not more than 1,000 mg/kg; and step (2): subjecting the reaction solution obtained after completion of the step (1) to the oxidation reaction at a temperature of not lower than 140° C. and not higher than 250° C.

2. The process for producing 2,5-furan dicarboxylic acid according to claim 1, wherein the noble metal is at least one metal selected from the group consisting of platinum group metals.

3. The process for producing 2,5-furan dicarboxylic acid according to claim 1, wherein the noble metal is platinum.

4. The process for producing 2,5-furan dicarboxylic acid according to claim 1, wherein the activated carbon-supported metal catalyst further comprises at least one metal (A) selected from the group consisting of bismuth and tin.

5. The process for producing 2,5-furan dicarboxylic acid according to claim 4, wherein a mass ratio of the noble metal to the metal (A) [noble metal/metal (A)] in the catalyst is not less than 1 and not more than 10.

6. The process for producing 2,5-furan dicarboxylic acid according to claim 1, wherein an amount of the oxygen fed until a time at which the step (1) is terminated is not less than 85 mol % and not more than 120 mol % on the basis of the 5-hydroxymethylfurfural charged.

7. The process for producing 2,5-furan dicarboxylic acid according to claim 1, wherein a flow rate of the oxygen in the step (1) is not less than 5 mol %/h and not more than 50 mol %/h on the basis of the 5-hydroxymethylfurfural charged, and a flow rate of the oxygen in the step (2) is not less than 5 mol %/h and not more than 60 mol %/h on the basis of the 5-hydroxymethylfurfural charged.

8. The process for producing 2,5-furan dicarboxylic acid according to claim 1, wherein prior to the step (1), the oxygen is previously added in an amount of not less than 5 mol % and not more than 60 mol % on the basis of the 5-hydroxymethylfurfural charged.

9. The process for producing 2,5-furan dicarboxylic acid according to claim 1, wherein an amount of the oxygen fed in the step (2) is not less than 15 mol % and not more than 50 mol % on the basis of the 5-hydroxymethylfurfural charged.

10. The process for producing 2,5-furan dicarboxylic acid according to claim 1, wherein a content of 5-hydroxymethylfurfural in a whole amount of the reaction solution upon initiation of the reaction in the step (1) is not less than 0.5% by mass and not more than 8.0% by mass.

11. The process for producing 2,5-furan dicarboxylic acid according to claim 1, wherein an amount of the activated carbon-supported metal catalyst used is controlled such that a mass of the noble metal used in the catalyst is not less than 0.5% by mass and not more than 10% by mass on the basis of a mass of 5-hydroxymethylfurfural.

12. The process for producing 2,5-furan dicarboxylic acid according to claim 1, wherein a temperature of the oxidation reaction in the step (1) is not lower than 80° C. and not higher than 100° C.

13. The process for producing 2,5-furan dicarboxylic acid according to claim 1, wherein a pressure of the reaction in the step (1) is not less than 0.15 MPa and not more than 0.8 MPa.

14. The process for producing 2,5-furan dicarboxylic acid according to claim 1, wherein an amount of the oxygen fed until the time at which the step (1) is terminated is not less than 90 mol % and not more than 120 mol % on the basis of 5-hydroxymethylfurfural charged.

15. The process for producing 2,5-furan dicarboxylic acid according to claim 1, wherein a temperature of the oxidation reaction in the step (2) is not lower than 155° C. and not higher than 220° C.

16. The process for producing 2,5-furan dicarboxylic acid according to claim 1, wherein a pressure of the reaction in the step (2) is not less than 0.2 MPa and not more than 0.98 MPa.

17. The process for producing 2,5-furan dicarboxylic acid according to claim 1, wherein an amount of the oxygen fed until the time at which the step (2) is terminated is not less than 124 mol % and not more than 138 mol % on the basis of 5-hydroxymethylfurfural charged.

18. The process for producing 2,5-furan dicarboxylic acid according to claim 1, wherein an amount of the oxygen fed in the step (2) is not less than 20 mol % and not more than 45 mol % on the basis of 5-hydroxymethylfurfural charged.

19. The process for producing 2,5-furan dicarboxylic acid according to claim 1, wherein a pH of the reaction solution upon charging in the step (1) is not less than 6.

20. The process for producing 2,5-furan dicarboxylic acid according to claim 1, wherein a pH of the reaction solution upon termination of the reaction in the step (2) is not more than 3.

* * * * *